(12) United States Patent
Hall et al.

(10) Patent No.: US 10,280,605 B2
(45) Date of Patent: May 7, 2019

(54) SPLIT TOILET BOWL FOR SEPARATING FECAL MATTER AND URINE FOR COLLECTION AND ANALYSIS

(71) Applicants: David R. Hall, Provo, UT (US); Daryl Wise, Provo, UT (US); John Christensen, Bluffdale, UT (US); Matthew Goodson, Yucaipa, CA (US); Joe Fox, Spanish Fork, UT (US)

(72) Inventors: David R. Hall, Provo, UT (US); Daryl Wise, Provo, UT (US); John Christensen, Bluffdale, UT (US); Matthew Goodson, Yucaipa, CA (US); Joe Fox, Spanish Fork, UT (US)

( * ) Notice: Subject to any disclaimer, the term of this patent is extended or adjusted under 35 U.S.C. 154(b) by 0 days.

(21) Appl. No.: 15/642,904

(22) Filed: Jul. 6, 2017

(65) Prior Publication Data

US 2019/0010689 A1  Jan. 10, 2019

(51) Int. Cl.

| | | |
|---|---|---|
| *E03D 11/13* | (2006.01) | |
| *A61B 10/00* | (2006.01) | |
| *E03D 11/02* | (2006.01) | |
| *G01N 33/493* | (2006.01) | |
| *G01N 33/483* | (2006.01) | |

(52) U.S. Cl.
CPC ......... *E03D 11/13* (2013.01); *A61B 10/0038* (2013.01); *E03D 11/025* (2013.01); *G01N 33/4833* (2013.01); *G01N 33/493* (2013.01)

(58) Field of Classification Search
CPC .......... E03D 11/13; E03D 11/02; A61G 7/02; A61G 7/047; A61B 10/0038; A61B 10/007

USPC ...... 4/450–455, 457, 340–341, 144.1, 144.2, 4/318, 319; 600/573–584
See application file for complete search history.

(56) References Cited

U.S. PATENT DOCUMENTS

| | | | | | |
|---|---|---|---|---|---|
| 904,293 | A | * | 11/1908 | Allen ...................... | A47K 11/02 4/463 |
| 1,002,508 | A | * | 9/1911 | Faust .................... | E03D 11/025 4/341 |
| 1,056,361 | A | * | 3/1913 | Podmore ............... | E03D 11/025 4/341 |
| 3,336,602 | A | * | 8/1967 | Kubit ........................ | E03D 1/26 4/301 |
| 3,965,497 | A | * | 6/1976 | Corsette .................. | E03D 9/038 4/227.5 |
| 4,197,598 | A | * | 4/1980 | Lemmon ................. | E03D 1/142 4/326 |
| 4,860,767 | A | * | 8/1989 | Maekawa ............... | E03D 11/00 600/573 |
| 5,073,500 | A | * | 12/1991 | Saito .................. | A61B 5/14507 4/300 |

(Continued)

*Primary Examiner* — Erin Deery

(57) ABSTRACT

The toilet bowl separately collects urine and feces for analysis or other uses. The toilet bowl includes a toilet bowl wall with at least two holes in it. The first hole is a fecal collection aperture positioned below a user where a user may defecate into it. The second hole is a urine collection orifice through which a user's urine may flow. The two holes may be separated by a ridge which may act like a dam to inhibit cross-contamination of collected feces and urine. Conduits may connect to the two holes to direct the waste into analytical devices or containers for additional uses including composters and digesters which produce clean energy.

9 Claims, 6 Drawing Sheets

(56) References Cited

U.S. PATENT DOCUMENTS

| | | | | |
|---|---|---|---|---|
| 5,548,850 A * | 8/1996 | Geeham | ............ | E03D 1/145 |
| | | | | 4/249 |
| 5,778,462 A * | 7/1998 | Bjorklund | ............ | A47K 11/02 |
| | | | | 4/463 |
| 6,087,182 A * | 7/2000 | Jeng | ............ | G01N 21/05 |
| | | | | 356/72 |
| 6,250,601 B1 * | 6/2001 | Kolar | ............ | E03C 1/057 |
| | | | | 251/129.04 |
| 2011/0004991 A1 * | 1/2011 | Tai | ............ | E03D 9/05 |
| | | | | 4/420 |
| 2015/0074893 A1 * | 3/2015 | Veros | ............ | E03D 1/00 |
| | | | | 4/313 |
| 2015/0342576 A1 * | 12/2015 | Hall | ............ | A61B 10/007 |
| | | | | 600/573 |

\* cited by examiner

SPLIT TOILET BOWL FOR SEPARATING FECAL MATTER AND URINE FOR COLLECTION AND ANALYSIS

BACKGROUND

Field of the Invention

This disclosure relates to methods of collecting and analyzing biological samples and biological waste.

Background of the Invention

Collecting fecal and urine samples according to traditional methods may be a messy, hazardous, inconvenient, and emotionally uncomfortable for the individual providing the sample. Typically, it is important to keep fecal and urine samples separate when they are analyzed to collect data relevant to a user's health. Other uses for separately collected urine and feces exist, including digesters for producing clean energy and water reclamation. A device is needed which may collect fecal and urine samples for storage or analysis which is convenient, discrete, sanitary, automated, and capable of inhibiting the cross-contamination of the feces and urine.

BRIEF SUMMARY OF THE INVENTION

The disclosed toilet bowl separately collects feces and urine for purposes that include analysis to gather health and diagnostic data, water reclamation, composting, and use in digesters. The toilet bowl may include a toilet bowl wall which has two holes in it. The holes may include a fecal collection aperture through which a user may deposit feces by defecating normally into the toilet bowl. The holes may further include a urine collection orifice through which the user's urine may flow. A ridge, which may be a raised area of the toilet bowl wall or a separate part, may act as a dam to inhibit cross-contamination of urine and feces.

Conduits may transmit waste from the holes to analytical devices which may analyze the waste to detect cross-contamination and/or to collect data that is relevant to a user's health status. The conduits may also transmit the waste to other devices for use of either feces or urine. For example, a conduit may transmit urine to a storage container where water may be reclaimed from the urine.

A conduit may recombine the separated urine and feces either for convenient disposal after analysis or for use in a digester which may produce clean energy. In the latter example, urine may be added to feces in defined amounts which are optimal for digester function.

The toilet bowl may also include sensors which detect cross-contamination of collected urine and feces. These may include capacitive sensors and optical sensors.

DETAILED DESCRIPTION OF THE INVENTION

Figure 1:
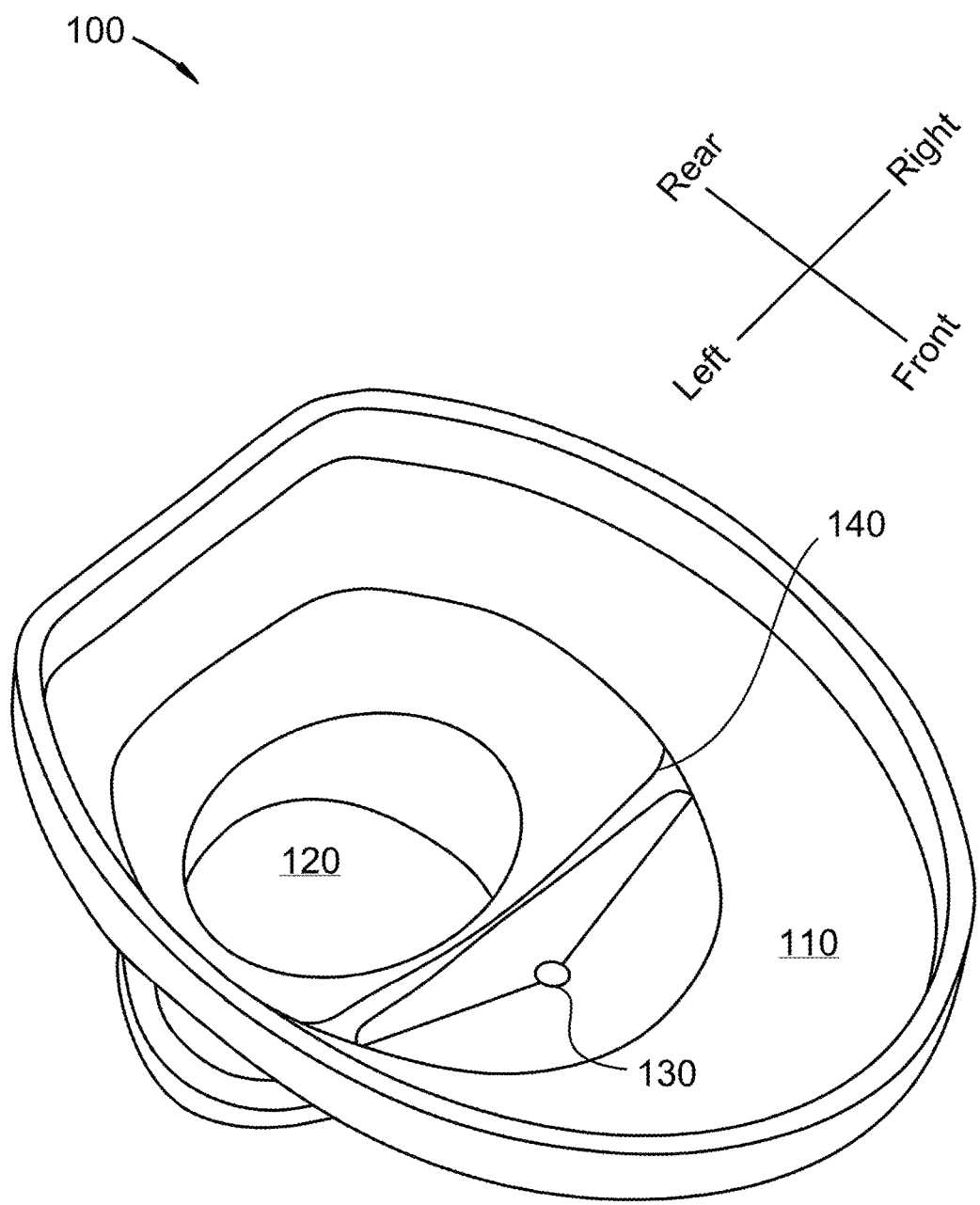
FIG. 1 illustrates an aerial view of an isometric drawing of an embodiment of the disclosed toilet bowl.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a toilet bowl which makes separate collection of urine and feces convenient, discreet, sanitary, and automated. The toilet bowl inhibits cross-contamination of urine and feces during collection. The separate urine and fecal samples may be subjected to analysis to gather data that may be used to assess a user's health and provide a diagnosis. In addition, the disclosed toilet bowl may provide greater flexibility for composting toilets/waste digesters, allowing moisture content to be more carefully controlled by separating out the urine, which could be treated separately or added to the solids in precise quantities.

The toilet bowl may include a bowl which separates urine and feces for independent collection. The bowl may include a toilet bowl wall that has a hole, referred to herein as a fecal collection aperture, within it. The fecal collection aperture may be positioned at the center of the toilet bowl or at least far enough from the front of the toilet bowl to collect feces as a user who is seated above the toilet bowl, for example on a toilet seat, defecates in the traditional manner. The feces may fall directly into the fecal collection aperture.

The toilet bowl may further include a second hole within the toilet bowl wall, referred to herein as a urine collection orifice, which may collect urine that is deposited into the toilet bowl. The urine collection orifice may be positioned further toward the front of the toilet bowl than the fecal collection aperture, a design which may deter fecal contamination of the urine collected by the urine collection aperture.

The toilet bowl wall may include a longitudinal raised area, referred to herein as a ridge. The ridge may be a raised part of the toilet bowl wall or a separate part connected to the toilet bowl wall. The ridge may be positioned between the urine collection orifice and the fecal collection aperture. The long side of the ridge may run across the width of the toilet bowl, for example, from left to right from the perspective of a user standing at the front of the toilet bowl. The ridge may act as a dam to impede urine which might otherwise flow into the fecal collection aperture, thus directing the urine toward the urine collection orifice. The ridge may also act as a barrier to obstruct feces which might otherwise enter the urine collection orifice.

Sensors may be present to detect cross-contamination of urine and feces. In some embodiments, the fecal collection aperture includes sensors, referred to herein as urine overflow sensors, on or in the toilet bowl wall surrounding the fecal collection orifice. These sensors may detect urine flow over the edge of the toilet bowl wall defining the fecal collection aperture and into the fecal collection aperture. In some embodiments, the urine overflow sensors may include capacitive sensors. Sensors, referred to herein as fecal contamination sensors, may be present elsewhere within the toilet bowl. In an example, the fecal contamination sensors may be located between the ridge and the front of the bowl. In some embodiments, the fecal contamination sensors include optical sensors which detect changes in spectral properties of urine in the event of fecal contamination.

Separation of urine and feces during collection may be important because of the purpose of the collection. The urine and feces may separately be collected for analysis to collect data relevant to the user's health status. Conduits may transmit the urine and feces into one or more urinalysis devices and one or more analytical devices capable of analyzing feces respectively. For example, a conduit, referred to herein as the urine collection conduit, may extend from the urine collection orifice to a urinalysis device. Consequently, the urine collection conduit delivers urine into the urinalysis device where measurements may be conducted that are relevant to a user's health. Similarly, a conduit, referred to herein as a fecal collection conduit, may extend from the fecal collection aperture to an analytical device capable of conducting measurements relevant to a user's health status.

In some embodiments, the urine collection conduit may include two optical windows through which a light source may direct light of a single wavelength or a range of wavelengths. A spectrometer may detect the spectra which has passed through the two optical windows and through the urine between them. These spectra may be used to detect fecal contamination in the urine or to provide data relevant to the user's health status.

The waste may be recombined after analysis for convenient disposal in the sewer system or composter. A conduit, referred to herein as a waste recombination conduit, may connect the urine collection conduit to the fecal collection conduit. The connection may be downstream of the urinalysis device and other analytical devices so that waste recombination occurs after the urine and feces are separately analyzed. The urine may be recombined with feces in controlled volumes using a controllable valve so that a defined amount of urine may be added to the feces. This may be important when the waste is to be sent to a digester for producing clean energy.

Alternatively, in some embodiments, the urine collection conduit may have no connection to the fecal collection conduit. Rather, the urine collection conduit may dispense the urine into a urine storage container. In an example, water from the stored urine may be reclaimed for later use.

Referring now to the drawings, FIG. 1 shows an aerial view of toilet bowl 100, an embodiment of the disclosure. A first axis shows the front and rear of toilet bowl 100. A second axis which is perpendicular to the first axis illustrates the meaning of the left and right sides of toilet bowl 100. The direction of left to right of the toilet bowl is meant by the "width" of the toilet bowl. Toilet bowl 100 includes a toilet bowl wall 110. Fecal collection aperture 120 within toilet bowl wall. A user may deposit feces through fecal collection aperture 120 while using toilet bowl 100 in the traditional manner. A smaller hole, urine collection orifice 130 is shown further toward the front of toilet bowl 100 than fecal collection aperture 120. Ridge 140 is a raised area in toilet bowl wall 100 which is positioned between fecal collection aperture 120 and urine collection orifice 130. As shown in toilet bowl 100, ridge 140 runs from right to left approximately parallel to an axis running across the width of toilet bowl 100. Ridge 140 acts as a physical barrier, like a wall or a dam, between fecal collection aperture 120 and urine collection orifice 130 to prevent mixing of urine and feces. A user may urinate in toilet bowl 100 in the traditional manner and ridge 140 may act as a dam to keep urine towards the front side of toilet bowl 100 and block the flow of urine into fecal collection aperture 120.

Figure 2:
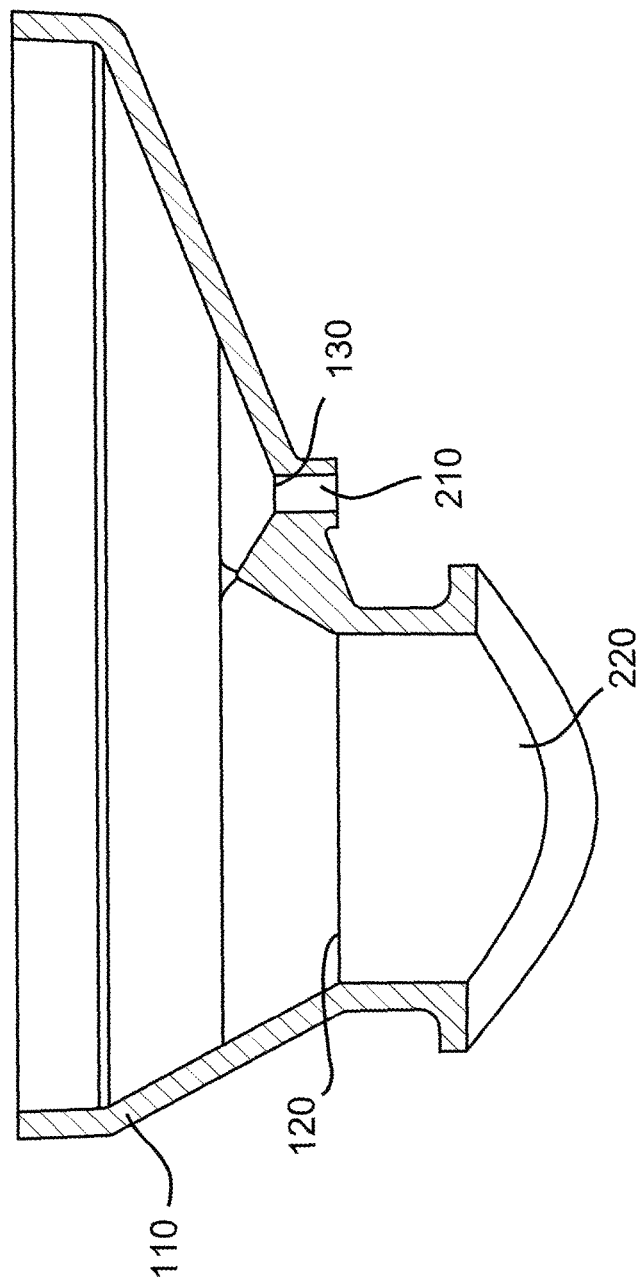
FIG. 2 illustrates a cross-sectional view of a schematic drawing of an embodiment of the disclosed toilet bowl.

FIG. 2 is a cross sectional view of toilet bowl 100 of FIG. 1. Toilet bowl wall 110 is shown as the hatched section around the edge of toilet bowl 100. Urine collection orifice 130 us shown toward the front (right side of FIG. 2) of toilet bowl 100. Urine collection conduit 210 extends downward from urine collection orifice 130. Urine may flow through urine collection orifice 130 which may be in fluid connection with urine collection conduit 210 and then to analytical devices, storage containers, or other destinations. Fecal collection aperture 120 is in communication with fecal conduit 220. Feces which enters fecal collection aperture 120 may be transported to an analytical device or other destination through fecal conduit 220.

Figure 3:
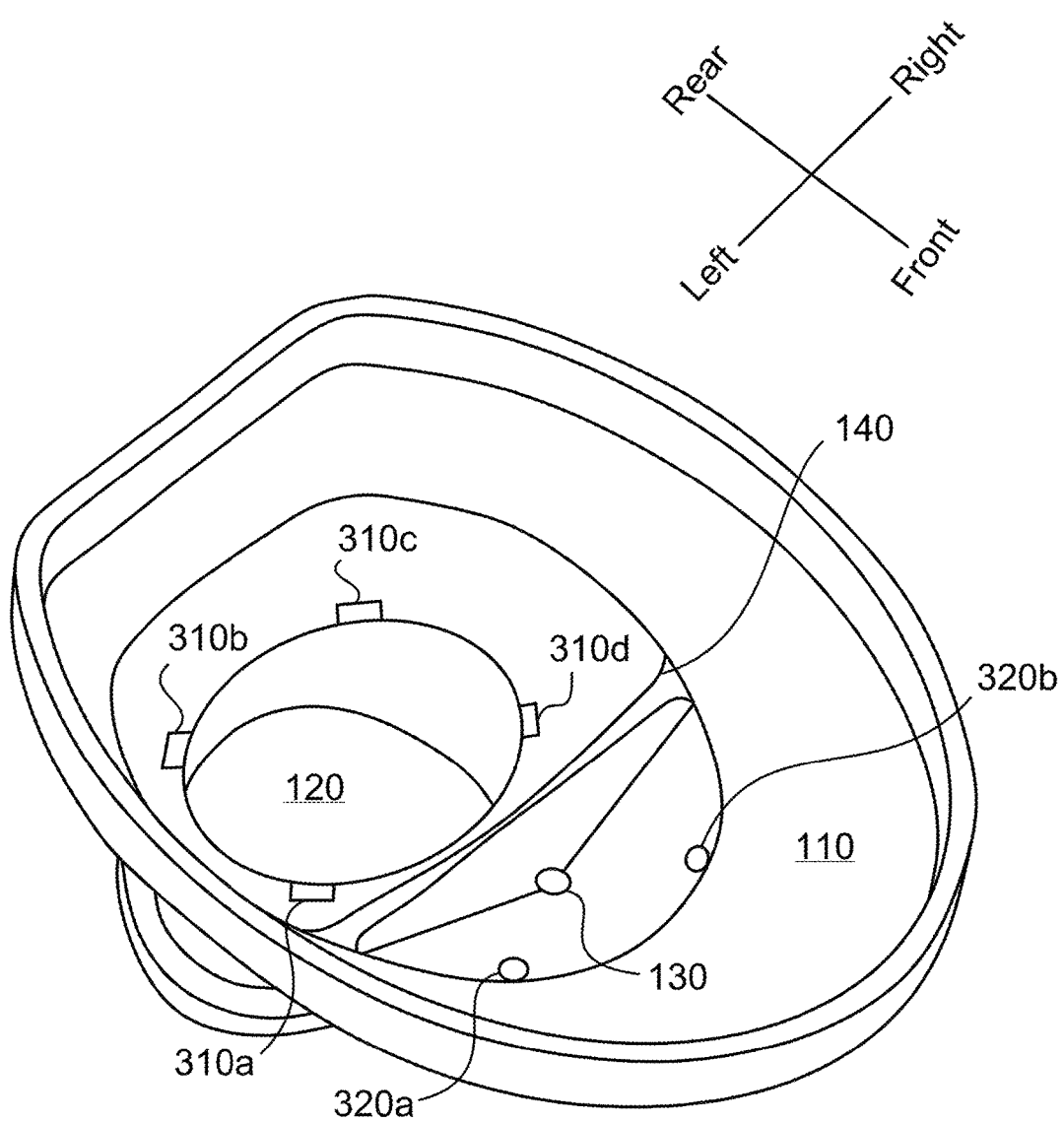
FIG. 3 illustrates an aerial view of an isometric drawing of an embodiment of the disclosed toilet bowl with sensors.

FIG. 3 illustrates an aerial view of another embodiment of a toilet bowl according to the disclosure. FIG. 3 illustrates a toilet bowl similar to toilet bowl 100 of FIG. 1. However, the embodiment of FIG. 3, further includes sensors 310a, 310b, 310c, and 310d surrounding fecal collection aperture 120. Sensors 310a-d may act as urine overflow sensors to detect urine passing into fecal collection aperture 120. In some embodiments, the urine overflow sensors may include one or more capacitive sensors. While FIG. 3 shows four urine overflow sensors, other embodiments may include one or any other number of urine overflow sensors.

The embodiment of FIG. 3 further includes fecal contamination sensors 320a and 320b. In the embodiment of FIG. 3, fecal contamination sensors 320a-b are positioned toward the front of the toilet bowl according to the axis shown to the right of the toilet bowl in FIG. 3. Furthermore, they are between the front of the toilet bowl and ridge 140. Fecal contamination sensors 320a-b may function to detect fecal contamination in the urine. In some embodiments, fecal contamination sensors 320a-b may include one or more optical sensors. While FIG. 3 shows two fecal contamination sensors, other embodiments may include one or any other number of fecal contamination sensors.

Figure 4:
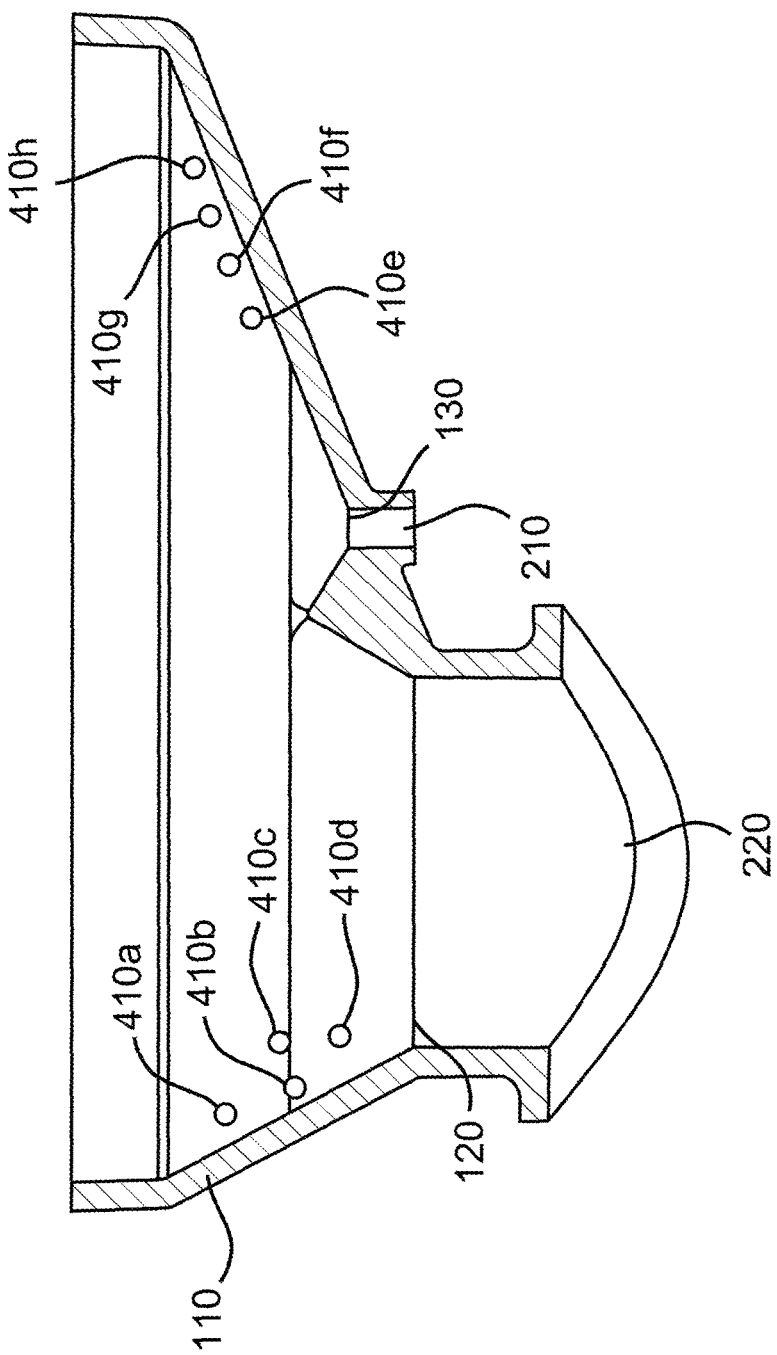
FIG. 4 illustrates a cross sectional view of a schematic drawing of an embodiment of the disclosed toilet bowl with cleansing agent dispensers.

FIG. 4 is a cross-sectional view of yet another embodiment of the disclosed toilet bowl. This embodiment is similar to toilet bowl 100 of FIG. 1. However, the embodiment of FIG. 4 includes cleansing agent dispensers 410a, 410b, 410c, 410d, 410e, 410f, 410g, and 410h. Cleansing agents, which may be stored in container having fluid connection to the disclosed toilet bowl, may be dispensed through cleansing agent dispensers 410a-g to rinse and cleanse the inner surface of toilet bowl wall 110. In addition to cleansing for hygienic purposes, the cleansing agent dispensers 410a-h may serve to remove urine and fecal samples from the toilet bowl between users as is prudent when urine and feces are analyzed to collect data to be used to assess the health of the user. Consequently, the cleansing agent dispensers 410a-h may prevent cross-contamination of samples collected for analysis. The cleansing agent may comprise a deodorant.

Figure 5:
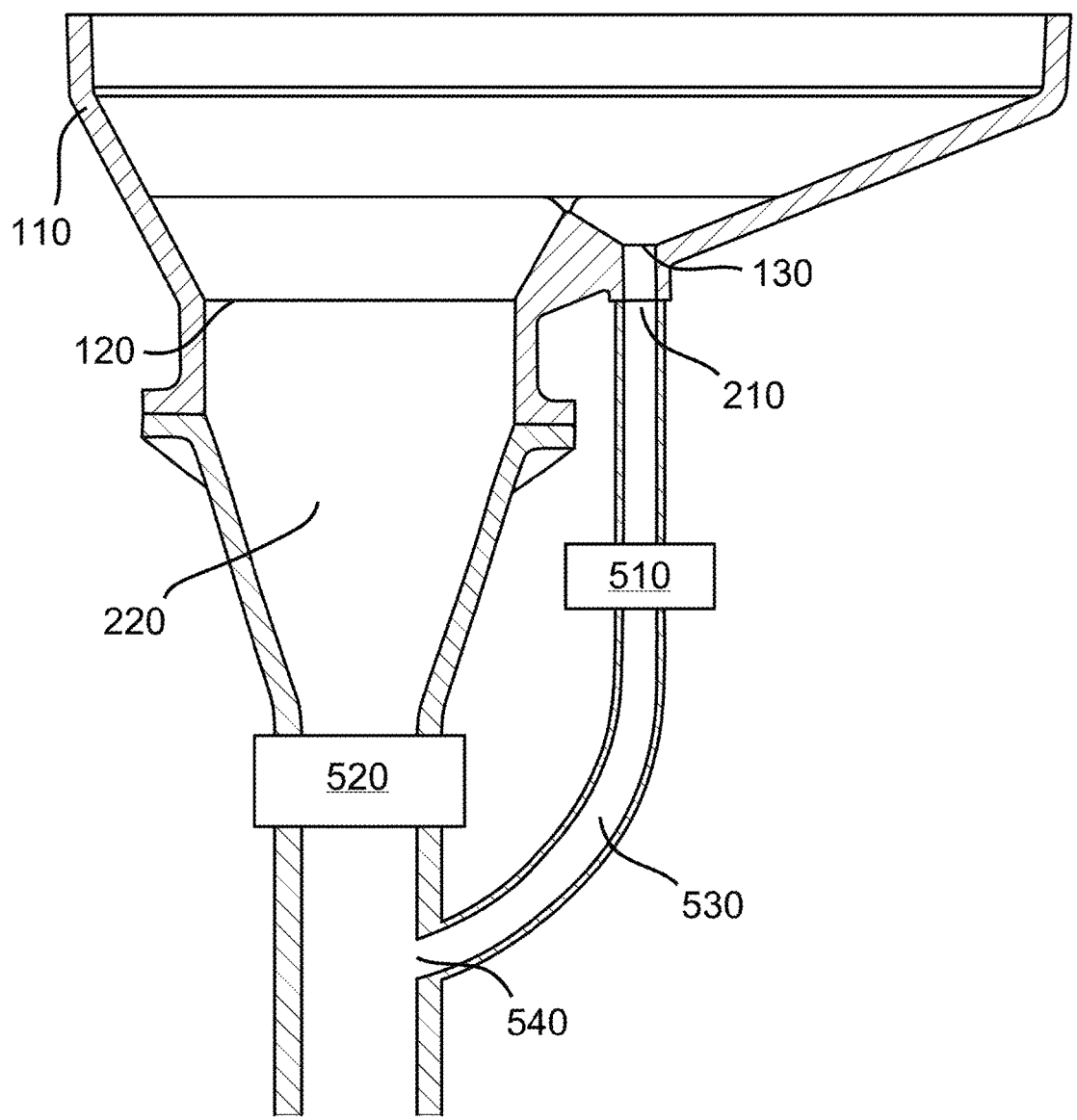
FIG. 5 illustrates a cross-sectional view of a schematic drawing of the disclosed toilet bowl including a fecal conduit, urine collection conduit, and urine reclamation conduit.

FIG. 5 shows a cross-sectional view of an embodiment of the disclosed toilet bowl which includes urinalysis device 510 and analytical device 520. Urine may flow through urine collection orifice 310 into urine collection conduit 210. Urine collection conduit 210 may transport the urine into urinalysis device 510 which may analyze the urine to collect data to be used to assess the user's health status or diagnose an illness.

Urinalysis device 510 may be a spectrometer. In some embodiments, the spectrometer detects ultraviolet, infrared, or visible light absorption spectra of the urine sample. In other embodiments, a spectrometer is included in the toilet bowl in addition to urinalysis device 510, the latter of which may be another type of clinically useful instrument which may analyze urine. The spectrometer may analyze the urine in addition to the analysis performed by urinalysis device 510. In some embodiments, the spectrometer may function to detect fecal contamination in the urine.

Figure 6:
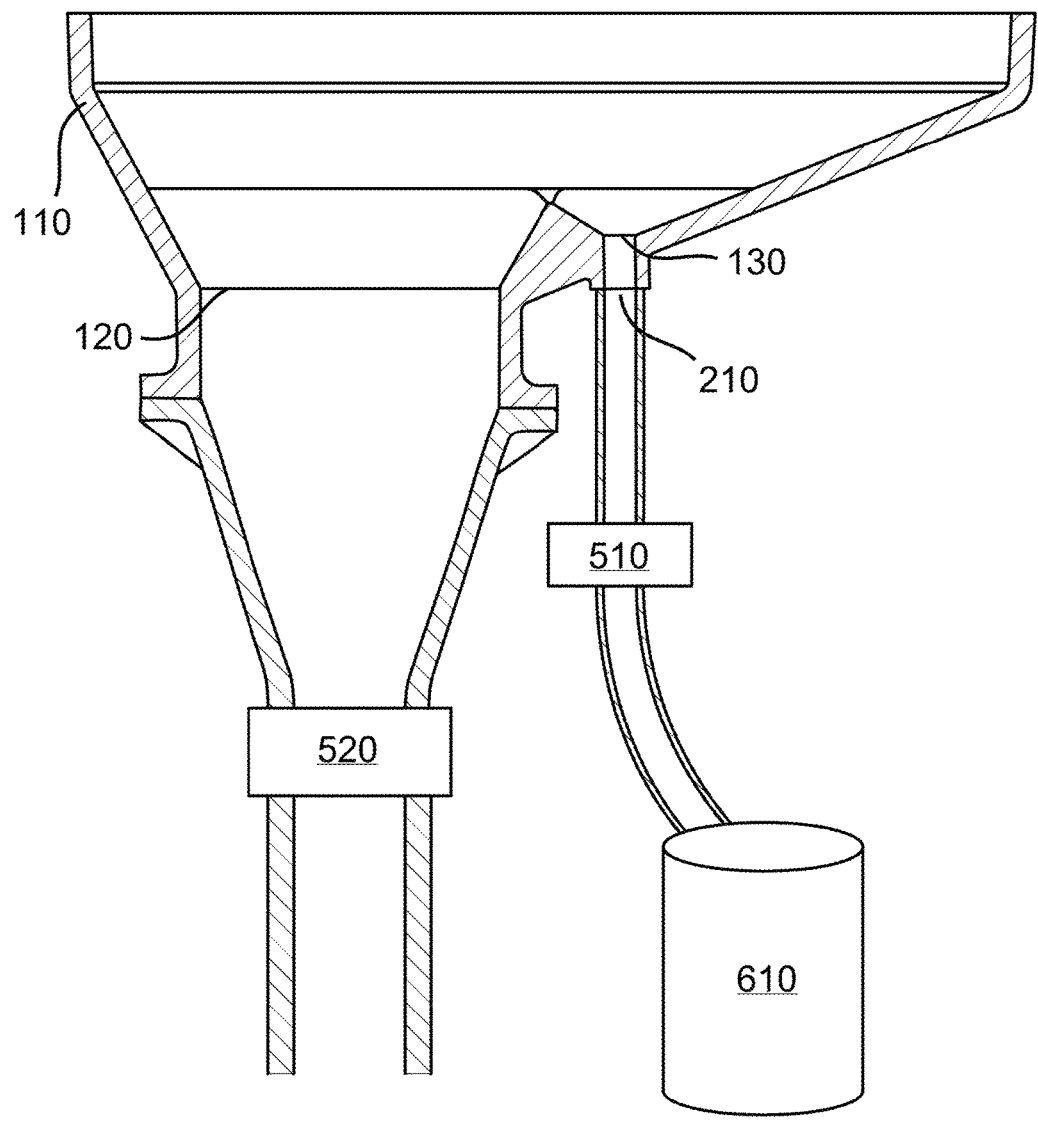
FIG. 6 illustrates a cross-sectional schematic view of a schematic drawing of the disclosed toilet bowl in which the urine collection conduit dispenses urine into a urine storage container.

In some embodiments, a section of urine collection conduit 210 may function as a sample chamber for the spectrometer. A first and a second optical window may be disposed on opposite sides of urine collection conduit 210. A light source may direct light of a single wavelength or a range or wavelengths through the first optical window and through the urine sample within urine collection conduit 210. Wavelengths of light not absorbed by the urine may be transmitted out through the second optical window. The spectrometer may detect the spectra transmitted through the second optical window. A conduit with two optical windows for a similar use is shown in FIG. 6 of U.S. patent application Ser. No. 15/632,807 filed on Jun. 26, 2017 which is hereby incorporated by reference.

Similar to the parts of the toilet bowl which collect and analyze urine, fecal collection aperture 120 is shown in communication with fecal conduit 220 which may transport feces into analytical device 520. Analytical device 520 may analyze the feces to collect data to be used to assess the user's health status of diagnose an illness.

The embodiment of FIG. 5 further includes waste recombination conduit 530. Waste recombination conduit 530 is shown distal in the system relative to urinalysis device 510 and connects to fecal conduit 220 at position 540 which is shown distal to analytical device 520. Consequently, in the embodiment shown in FIG. 5, urine and feces are analyzed by urinalysis device 510 and analytical device 520 respectively then recombined for disposal into a digester for energy use or into the sewer system.

FIG. 6 is a cross-sectional view of yet another embodiment of the disclosed toilet bowl. The embodiment of FIG. 6 is similar to that of FIG. 5. However, after the urine leaves urinalysis device 510, urine collection conduit 210 transports the urine into urine storage container 610. The urine stored in urine storage container 610 may be used for purposes including adding urine to a composter or digester in controlled amounts to produce fertilizer or clean energy or to reclaim water.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein

We claim:

1. A toilet bowl for separately collecting urine and feces comprising:
 a. a bowl, the bowl comprising:
  i. a toilet bowl wall, the toilet bowl wall comprising:
   1. a fecal collection aperture;
   2. a fecal conduit, wherein the fecal conduit is in communication with the fecal collection aperture, and wherein the fecal conduit extends downward from the fecal collection aperture;
   3. a urine collection orifice, wherein the urine collection orifice is disposed toward a front of the toilet bowl relative to the fecal collection aperture;
   4. a urine collection conduit, wherein the urine collection conduit extends downward from the urine collection orifice, wherein the urine collection conduit is in fluid communication with a urinalysis device;
   5. a waste recombination conduit, wherein the waste recombination conduit connects the urine collection conduit and the fecal conduit at a point which is distal to the urinalysis device, and wherein the waste recombination conduit comprises a controllable valve configured to release a defined amount of urine to into the fecal collection conduit; and
   6. a ridge, wherein the ridge is defined by a raised section in the toilet bowl wall, and wherein the ridge is between the fecal collection aperture and the urine collection orifice and approximately parallel to an axis running across the width of the bowl.

2. The toilet bowl of claim 1, further comprising at least one urine overflow sensor, wherein the at least one urine overflow sensor is disposed on the toilet bowl wall and is adjacent to the fecal collection orifice.

3. The toilet bowl of claim 2, wherein the at least one urine overflow sensor comprises at least one capacitive sensor.

4. The toilet bowl of claim 1, further comprising at least one fecal contamination sensor, wherein the at least one fecal contamination sensor is disposed within the toilet bowl and between the ridge and the front of the toilet bowl.

5. The toilet bowl of claim 4, wherein the at least one fecal contamination sensor comprises at least one optical sensor.

6. The toilet bowl of claim 1, wherein the urinalysis device comprises a spectrometer, wherein the urine collection conduit defines a sample chamber within the spectrometer, wherein the urine collection conduit comprises a first and a second optical window, wherein the first optical window is disposed within a first side of the urine collection conduit, and wherein the second optical window is disposed within a second side of the urine collection conduit.

7. The toilet bowl of claim 6, wherein the spectrometer detects ultraviolet, infrared, or visible light absorption spectra.

8. The toilet bowl of claim 1, further comprising one or more cleansing agent dispensers, wherein the one or more cleansing agent dispensers dispense one or more cleansing agents onto the toilet bowl wall.

9. The toilet bowl of claim 8, wherein the one or more cleansing agents comprises a deodorant.

* * * * *